(12) United States Patent
Schuelke et al.

(10) Patent No.: US 11,592,373 B2
(45) Date of Patent: Feb. 28, 2023

(54) ELECTROCHEMICAL METHODS FOR SAMPLE PRETREATMENT FOR METALS DETERMINATION AND RELATED APPARATUS

(71) Applicants: BOARD OF TRUSTEES OF MICHIGAN STATE UNIVERSITY, East Lansing, MI (US); Fraunhofer USA, Plymouth, MI (US)

(72) Inventors: Thomas Schuelke, Pinckney, MI (US); Cory A. Rusinek, Okemos, MI (US); Michael Becker, East Lansing, MI (US); Mary Ensch, Belleville, MI (US)

(73) Assignees: BOARD OF TRUSTEES OF MICHIGAN STATE UNIVERSITY, East Lansing, MI (US); Fraunhofer USA, Plymouth, MI (US)

( * ) Notice: Subject to any disclaimer, the term of this patent is extended or adjusted under 35 U.S.C. 154(b) by 469 days.

(21) Appl. No.: 16/697,417

(22) Filed: Nov. 27, 2019

(65) Prior Publication Data

US 2020/0173891 A1 Jun. 4, 2020

Related U.S. Application Data

(60) Provisional application No. 62/773,494, filed on Nov. 30, 2018.

(51) Int. Cl.
*G01N 1/40* (2006.01)
*B01L 3/00* (2006.01)
*G01N 33/487* (2006.01)

(52) U.S. Cl.
CPC ............... *G01N 1/40* (2013.01); *B01L 3/502* (2013.01); *G01N 33/48714* (2013.01); *B01L 2300/0663* (2013.01); *B01L 2400/0415* (2013.01); *G01N 2001/4038* (2013.01)

(58) Field of Classification Search
CPC ............... G01N 1/40; G01N 33/48714; G01N 2001/4038; B01L 3/502; B01L 2300/0663; B01L 2400/0415
See application file for complete search history.

(56) References Cited

U.S. PATENT DOCUMENTS

| 2005/0208670 | A1 | 9/2005 | Wittenberg et al. |
| 2010/0320423 | A1* | 12/2010 | Tajima ............... C04B 35/52 |
| | | | 252/509 |
| 2013/0299361 | A1 | 11/2013 | Wylie et al. |
| 2015/0008139 | A1 | 1/2015 | Saffron et al. |
| 2018/0217087 | A1 | 8/2018 | Swain et al. |

FOREIGN PATENT DOCUMENTS

| DE | 10 2015 110 179 B3 | 12/2016 |
| WO | WO-2009/123645 A1 | 10/2009 |
| WO | WO-2017/027477 A1 | 2/2017 |

\* cited by examiner

*Primary Examiner* — Christopher Adam Hixson
(74) *Attorney, Agent, or Firm* — Marshall, Gerstein & Borun LLP

(57) ABSTRACT

The disclosure relates to a method for pretreating a sample for metals determination. The method includes: providing an aqueous sample mixture comprising a sample containing or suspected of containing one or more metals for detection; contacting the aqueous sample mixture with a first electrode (anode) comprising electrically conducting boron-doped diamond (BDD); electrically contacting the aqueous sample mixture with a second electrode (cathode); applying an electrical potential between the first electrode and the second electrode (i) to provide an electrical current therebetween and through the aqueous sample mixture, (ii) to generate hydroxyl ion ($OH^-$) species at the first electrode, (iii) to oxidize and free the one or more metals for detection in the sample, thereby forming a pretreated aqueous sample comprising free metal ions in aqueous solution and corresponding to the one or more metals in the original sample; and withdrawing the pretreated aqueous sample comprising the free metal ions in aqueous solution. The pretreated aqueous sample can be analyzed for metal content using any desired conventional analysis technique.

25 Claims, 5 Drawing Sheets

ELECTROCHEMICAL METHODS FOR SAMPLE PRETREATMENT FOR METALS DETERMINATION AND RELATED APPARATUS

CROSS REFERENCE TO RELATED APPLICATION

Priority is claimed to U.S. Provisional Patent Application 62/773,494, filed Nov. 30, 2018, the entire disclosure of which is incorporated herein by reference.

STATEMENT OF GOVERNMENT INTEREST

None.

BACKGROUND OF THE DISCLOSURE

Field of the Disclosure

The disclosure relates to a method for pretreating a sample for metals determination. An aqueous sample mixture is electrochemically treated with a boron-doped diamond (BDD) electrode to oxidize and free one or more metals that can be present in the sample as free metal ions. The pretreated sample can be analyzed by conventional metals analysis techniques.

Background

Metals toxicology and the associated health effects is a problem facing many communities across the world. Due to the vast number of exposure routes, the issue has been brought to the forefront of industry and government. As such, the call for advancements in research and development to generate tangible solutions to assess exposure has never been stronger.

In current practice, metals toxicology assessment is typically completed through blood sampling. Samples are then sent to an external lab where trained professionals execute a variety of accurate, yet expensive measurements such as inductively coupled plasma-mass spectrometry (ICP-MS) and/or graphite furnace atomic absorption spectroscopy (GF-AAS). In order to complete any analysis, however, the blood samples must be pre-treated to break down any organic constituents in the sample of interest, leaving only the metal ions behind. This is achieved via microwave-assisted digestion (MAD) techniques or via an acid digestion with heat. While these methods are effective, microwave digestion systems are also expensive (>$30,000) and acid/heat digestion, while inexpensive, can take over 5 hours. Additionally, in most cases these sample pre-treatment procedures also require larger sample volumes (about 1 mL). In the case of infants where blood lead (Pb) levels (BLLs) are routinely checked at the 12-month check-up appointment, blood sample volumes must be kept to a minimum.

While the aforementioned techniques are useful and precise, the length of turnaround time for laboratory results generates a significant hindrance in medical assessment. As a result, a technique or method which expedites this process without compromising on sensitivity or precision is desired. One such system is available on the market, the LEAD-CARE system available from Magellan Diagnostics. This system uses small sample volumes and claims the ability to measure blood lead (Pb) levels (BLL) in under 5 minutes. In some cases, however, the system may result in an underestimation of the BLL, potentially leading to a misdiagnosis of a health risk.

SUMMARY

In one aspect, the disclosure relates to a method for pretreating a sample for metals determination, the method comprising: providing an aqueous sample mixture comprising a sample containing or suspected of containing one or more metals for detection; contacting the aqueous sample mixture with a first electrode (anode) comprising electrically conducting boron-doped diamond (BDD); electrically contacting the aqueous sample mixture with a second electrode (cathode); applying an electrical potential between the first electrode and the second electrode (i) to provide an electrical current therebetween and through the aqueous sample mixture, (ii) to generate hydroxyl ion ($OH^-$) species at the first electrode, (iii) to oxidize and free the one or more metals for detection in the sample, thereby forming a pretreated aqueous sample comprising free metal ions in aqueous solution and corresponding to the one or more metals in the original sample; and withdrawing the pretreated aqueous sample comprising the free metal ions in aqueous solution.

The aqueous sample mixture includes water as the sample medium. The water can include water present in the original sample (e.g., a biological fluid sample, a wastewater sample, a groundwater sample) and/or water added to the sample prior to pretreatment (e.g., water for dilution of an original liquid sample or for mixing with an original solid or soil sample, such as including an acid therein). During pretreatment, the aqueous sample mixture is in direct physical contact with the first electrode (anode) such that metals present in the sample in various forms are subject to liberation from binding species and/or oxidation by hydroxyl ion ($OH^-$) species generated at the first electrode (anode) to form corresponding metal ions. Similarly during pretreatment, the aqueous sample mixture is in electrical contact with the second electrode (cathode) such that there can be a current passing from the two electrodes and through the aqueous sample mixture. There can be, but need not be, direct physical contact between the second electrode (cathode) and the aqueous sample mixture. A single-cell (or single-compartment) electrochemical cell arrangement generally includes direct physical contact between the second electrode (cathode) and the aqueous sample mixture. A divided-cell (or multi-compartment) electrochemical cell arrangement generally includes electrical contact only between the second electrode (cathode) and the aqueous sample mixture, the second electrode being physically separated from the aqueous sample mixture. After pretreatment, the pretreated aqueous sample containing free metal ions can be withdrawn from an electrochemical cell or other vessel/apparatus including the first and/or second electrodes therein.

In another aspect, the disclosure relates to a system for sample pretreatment and metals determination, the system comprising: an electrochemical cell defining an oxidation reaction volume adapted to receive an aqueous sample mixture comprising a sample containing or suspected of containing one or more metals for detection, the electrochemical cell comprising (i) a first electrode (anode) positioned in the oxidation reaction volume and comprising electrically conducting boron-doped diamond (BDD), and (ii) a second electrode (cathode) positioned to be in electrical contact with the oxidation reaction volume (e.g., in the oxidation reaction volume in a single cell apparatus, via a supporting electrolyte and membrane in a divided cell apparatus); a metals detection apparatus in fluid communication with the oxidation reaction volume of the electrochemical cell; optionally a power supply in electrical connection with the first electrode and the second electrode, the power supply being adapted to apply an electrical potential between the first electrode and the second electrode; and optionally a sample reservoir in fluid communication with the oxidation reaction volume, the sample reservoir being adapted to receive the aqueous sample mixture therein and deliver the aqueous sample mixture to the oxidation reaction volume. The electrochemical cell is capable of performing the method for pretreating a sample according to any of the various embodiments when an aqueous sample mixture is delivered thereto and electric potential is applied to the electrodes. The pretreated aqueous sample formed in the electrochemical cell is then fed to the metals detection apparatus (e.g., ICP-MS, GF-AAS, voltammetric detection apparatus) to identify and quantify the various metal species present in the pretreated aqueous sample and corresponding original sample.

Various refinements of the disclosed methods and systems for pretreating a sample for metals determination are possible.

In a refinement, the sample comprises a biological sample, for example a biological fluid or tissue from a human, other animal, or plant. In a particular refinement, the biological sample is selected from the group consisting of a blood sample (e.g., whole blood, serum), a saliva sample, and a urine sample.

In another particular refinement, the biological sample comprises a protein. For example, the protein can be a metalloprotein or other metal-binding protein typically found in blood or other biological material, which metalloprotein can bind one or more metals of interest such as cobalt, copper, iron, manganese, nickel, zinc. Transferrin is an example of a glycoprotein for bound iron ($Fe^{3+}$) that is normally present in blood. In addition to proteins, biological samples can also include other chelating agents or metal-binding compounds such as citric acid.

In a refinement, the sample comprises an environmental sample, for example, a solid or liquid sample from the environment to be tested for metals, such as for the purpose of compliance with environmental regulations. In a particular refinement, the environmental sample is selected from the group consisting of groundwater, surface water (e.g., fresh or saltwater such as lake, pond, river, stream, swamp, sea, ocean), wastewater (e.g., domestic, commercial, or industrial, such as a stream to/from a wastewater treatment plant), soil, sludge, sediment, concrete, leachate, and combinations thereof. When the environmental sample includes a solid material, it is mixed or otherwise diluted with water to form the corresponding aqueous sample mixture, such as with the solid material suspended therein.

In another particular refinement, the environmental sample comprises a chelating agent. The environmental sample can include metal-binding or metal-complexing agents such as a weak acid, for example including ethylenediaminetetraacetic acid (EDTA), citric acid, fulvic acids, or other chelating agents. An environmental sample similarly can include one or more metal-binding components typical of a biological sample (e.g., metalloprotein or other metal-binding protein as described above), for example when the environmental sample includes wastewater or other biological material or waste therein.

In a refinement, the aqueous sample mixture is substantially free from solids. For example, the aqueous sample mixture can contain less than 10 wt. % solids, such as suspended or dispersed (e.g., non-dissolved) solids, in particular less than 0.1, 1, 2, 5, or 10 wt. % solids. Alternatively or additionally, the aqueous sample mixture can include water as its primary components, such as having at least 80, 90, 95, 98, or 99 wt. % water.

In a refinement, the aqueous sample mixture has a pH value of 4 or less. The pH value is suitably 2 or less or 4 or less. The pH can be adjusted to the desired value by adding a suitable amount of strong (e.g., mineral) acid such as hydrochloric acid, sulfuric acid, nitric acid, phosphoric acid, or another acid such as acetic acid. For example, the sample can be diluted with or have added thereto an acid having a concentration generally ranging from 0.1 M to 5 M. In cases where the sample is naturally acidic and has a sufficiently low pH for electrochemical oxidation of metals in its natural state, no acid need be added. The pH value can represent the initial pH value of the aqueous sample mixture before and/or during electrochemical oxidation. During the pretreatment process, formation of the hydroxyl ions at the BDD electrode can form corresponding peracid species in the aqueous sample mixture being treated. In a divided cell configuration, the pH value can reduce over time during pretreatment as a result of hydrogen ion (H+) generation from water oxidation. The aqueous sample mixture generally does not need to include a supporting electrolyte in solution (although such is possible), the presence of the acid in the aqueous sample mixture is generally sufficient for electrical conductivity of the sample mixture.

In a refinement, the one or more metals for detection are selected from the group consisting of aluminum (Al), antimony (Sb), arsenic (Ar), barium (Ba), bismuth (Bi), cadmium (Cd), chromium (Cr), cobalt (Co), copper (Cu), iron (Fe), gallium (Ga), germanium (Ge), gold (Au), indium (In), lead (Pb), manganese (Mn), mercury (Hg), nickel (Ni), silver (Ag), thallium (Tl), tin (Sn), vanadium (V), zinc (Zn), and combinations thereof. The foregoing metals are illustrative and the method can more generally used to electrochemically oxidize any metal of interest to a corresponding free, ionic form for subsequent detection and/or quantitation by a suitable detection method. Any combination of the foregoing metals in any amounts and forms can be present in the original sample.

In a refinement, the sample contains the one or more metals for detection; and at least 80 wt. % of total metals present in the original sample in any form are present in the pretreated aqueous sample as free metal ions. Suitably at least 80, 85, 90, 95, or 98 wt. % and/or up to 90, 95, 98, 99, or 100 wt. % of metals originally present are converted to free metal ions in aqueous solution in the final pretreated sample. The foregoing ranges can individually apply to all metal species present collectively as well as individual species. The metals can generally be in any form in the original sample material, for example including free or bound, and ionic or non-ionic, with the purpose of the pretreatment method being to convert the substantially majority of metals to an ionic form where they are free in aqueous solution, which permits them to be detected and/or quantitated with a variety of conventional analytical techniques. In contrast, when in bound or non-ionic form, the metals are generally in unsuitable form for subsequent detection, leading to possible false negative results or substantially lower-than-actual measured concentrations. The metals can be in elemental or metallic form, for example as a pure metal or metal alloy blend. The metals can be in molecular form, for example being covalently or ionically bound to one or more other non-metal atoms (e.g., metal oxides, metal salts, etc. which can be soluble or insoluble in water). The metals can be in an ionic or non-ionic form, but in a chelated, complexed, or otherwise bound form, for example in combination with a metal-binding protein, chelating agent, or other metal-binding agent. The metals can be in a free ionic form in the original sample, in which case they are already in suitable form for subsequent metals analysis, but there is no adverse effect of having them initially present in such form.

In a refinement, the boron-doped diamond (BDD) of the first electrode has a carbon:boron (C:B) atomic ratio ranging from 100:1 to 100000:1. The BDD suitably has a carbon:boron (C:B) atomic ratio of at least 100:1, 200:1, 500:1, or 1000:1 and/or up to 1000:1, 2000:1, 5000:1, 10000:1, or 100000:1. Relatively lower dopant levels of boron can increase the relative $sp^3$ content of the BDD, while relatively higher dopant levels of boron can increase degree of hydroxyl ion ($OH^-$) species generation at the anode for target analyte oxidation. The BDD generates the hydroxyl ion species at the anode at relatively high voltages and current densities, which species in turn scavenge chelating or other metal-binding groups in the sample, decomposing such groups as well as other proteinaceous, organic, or non-metal materials into gaseous, water-soluble, or ionic species (e.g., $CO_2$, $CO_3^{2-}$, $N_2$, $NO_2^-$ $NH_3$, $NO_3^-$, $ClO_3^-$, $ClO_4^-$, S-containing gases). Decomposition of such metal-binding groups releases any metals therein, allowing the hydroxyl ion species to oxidize the metals (i.e., if not already in the final oxidized form) as well as other metals originally present in the sample in unbound form). The BDD is suitably free of other dopants (e.g., nitrogen, phosphorous), generally having no such other dopants added or being present at other than impurity-level concentrations (e.g., up to 1:1000, 1:10000, or 1:100000 atomic ratio of other dopant or impurity:carbon). The BDD suitably has a microcrystalline morphology. The BDD can be formed/deposited by chemical vapor deposition on a substrate, for example using a deposition source gas including a carbon source (e.g., methane), a boron source (e.g., diborane), and diluent (e.g., one or more of hydrogen, argon, etc.). The chemical vapor deposition (CVD) can be any suitable process, for example a microwave-assisted plasma CVD process.

In a refinement, the first electrode further comprises a substrate upon which the boron-doped diamond (BDD) is coated. The substrate is generally a metal or other material suitable for deposition of BDD thereon, for example including niobium, molybdenum, tantalum, tungsten, or silicon. The substrate can have any desired shape, but it suitably has a relatively high surface area-to-volume ratio to correspondingly provide a relatively higher BDD surface area, hydroxyl ion ($OH^-$) species generation rate, and oxidation rate. For example, the substrate can have a mesh or perforated plate structure to increase surface area and allow circulation of the aqueous sample mixture through the first electrode and in contact with the BDD thereon during operation. In other embodiments, the substrate can include a porous material, for example a porous form of a material suitable for deposition of BDD thereon as described above. In other embodiments, the substrate can be omitted and the first electrode can include a free-standing BDD film or material.

In a refinement, the aqueous sample mixture is in direct physical contact with both the first electrode and the second electrode during oxidation. This can represent a single-cell (or single-compartment) electrochemical cell in which the aqueous sample mixture is in direct physical contact and (accordingly) electrical contact with both electrodes. The polarity can be switched/cycled between the two electrodes such that each electrode periodically functions as the anode for hydroxyl ion generation and metal oxidation. In such cases, the second electrode suitably additionally includes electrically conducting BDD, for example as a deposition or other coating on a substrate as described for the first electrode.

In a refinement, the aqueous sample mixture is in direct physical contact with the first electrode, and the aqueous sample mixture is not in direct physical contact with the second electrode during oxidation. This can represent a divided cell (or multi-compartment) electrochemical cell in which the aqueous sample mixture is physically isolated from the second electrode, but electrical current can pass through an electrolyte in the second electrode cell, through a membrane, and into the aqueous sample mixture in first electrode cell. The second electrode need not (and suitably does not) include any BDD. The second electrode can be formed from any desired electrically conductive material such as stainless steel, silver, nickel, platinum, carbon, lead, lead dioxide, etc. The second cell or compartment which contains the second electrode generally further includes a liquid (e.g., water or water-containing liquid) including a supporting electrolyte such as sodium sulfate, potassium sulfate, sodium nitrate, potassium nitrate, sodium carbonate, or the like. The membrane can be an electrically conductive membrane such as a sulfonated tetrafluoroethylene fluoropolymer (e.g., NAFION) or other (sulfonated) polymer based on polypropylene, poly(tetrafluoroethylene) (PTFE)-type polymer.

In a refinement, the withdrawn pretreated aqueous sample further comprises one or more non-metal polyatomic ions. The polyatomic ions are suitably anions that are decomposition products from proteinaceous, organic, or non-metal materials in the original sample. Examples include ionic species such as $CO_3^{2-}$, $NO_3^-$, $PO_4^{2-}$ and $ClO_4^-$. The withdrawn pretreated aqueous sample can further include dissolved, water-miscible components such as liquids (e.g., $NH_3$) and/or dissolved gases (e.g., $CO_2$, $N_2$). Such species generally do not interfere with and need not be removed prior to conventional metals analysis techniques. As a result of such decomposition of other non-metal materials in the original sample, the withdrawn pretreated aqueous sample can be directly analyzed in its form as withdrawn (e.g., without the need for further filtering, separation, purification, or other treatment).

In a refinement, the free metal ions in aqueous solution in the pretreated aqueous sample are not subsequently reduced to an elemental metallic form, such as one or more metal elements in a zero oxidation state as a pure metal or alloy blend of multiple metals. Such reduction is suitably not performed or is otherwise prevented/avoided prior to withdrawal of the pretreated aqueous sample (e.g., in an electrochemical cell or other vessel/apparatus including the first and/or second electrodes therein) and/or prior to analysis of the withdrawn pretreated aqueous sample for metal content (i.e., detection of the metal ions in solution). In such embodiments, the pretreated aqueous sample or corresponding cell/vessel is suitably not contacted with/does not contain a reducing electrode. In a single-cell electrochemical cell, cycling or reversal of polarity between the first and second electrode can be performed to keep the free metal ions in solution and not plated or otherwise reduced on an electrode surface. In a divided-cell electrochemical cell, the presence membrane can keep the metal ions confined in the first electrode (anode) compartment and accordingly prevent deposition or plating of the metal ions on the second electrode in the other compartment.

In a refinement, the aqueous sample mixture has a volume in a range from 10 µl to 500 µl, for example at least 10, 20, 50, or 100 µl and/or up to 50, 100, 200, 300, or 500 µl. More generally, the pretreatment method can be performed on microfluidic scale in which a very small sample volume is used for pretreatment and analysis, whether as batch sample aliquot or as a part of a continuous flow device. The low sample volumes increase pretreatment speed and reduce total analysis time.

In a refinement, the method further comprises analyzing the withdrawn pretreated aqueous sample for metal content. This can be performed by using any suitable conventional technique for metals detection, for example which uses an aqueous solution of metal ions as an input to an analytical apparatus or system. Representative examples of such apparatus and/or techniques include inductively coupled plasma-mass spectroscopy (ICP-MS), inductively coupled plasma-atomic emission spectroscopy (ICP-AES), graphite furnace-atomic absorption spectroscopy (GF-AAS), electrochemical detection via anodic or cathodic stripping voltammetry (ASV/CSV), etc. The withdrawn pretreated aqueous sample suitably can be used as-is for subsequent metals detection and without separation or purification of the pretreated aqueous sample prior to metals analysis.

In a refinement, the method further comprises withdrawing a gaseous byproduct stream, such as from an electrochemical cell or other vessel/apparatus including the first and/or second electrodes therein. The gaseous byproducts are suitably gases that are decomposition products from proteinaceous, organic, or non-metal materials in the original sample. Examples include species such as $CO_2$, $N_2$, S-containing gases, etc.

While the disclosed methods, apparatus, and compositions and are susceptible of embodiments in various forms, specific embodiments of the disclosure are illustrated (and will hereafter be described) with the understanding that the disclosure is intended to be illustrative, and is not intended to limit the claims to the specific embodiments described and illustrated herein.

BRIEF DESCRIPTION OF THE DRAWINGS

For a more complete understanding of the disclosure, reference should be made to the following detailed description and accompanying drawings wherein.

DETAILED DESCRIPTION

Figure 1A:
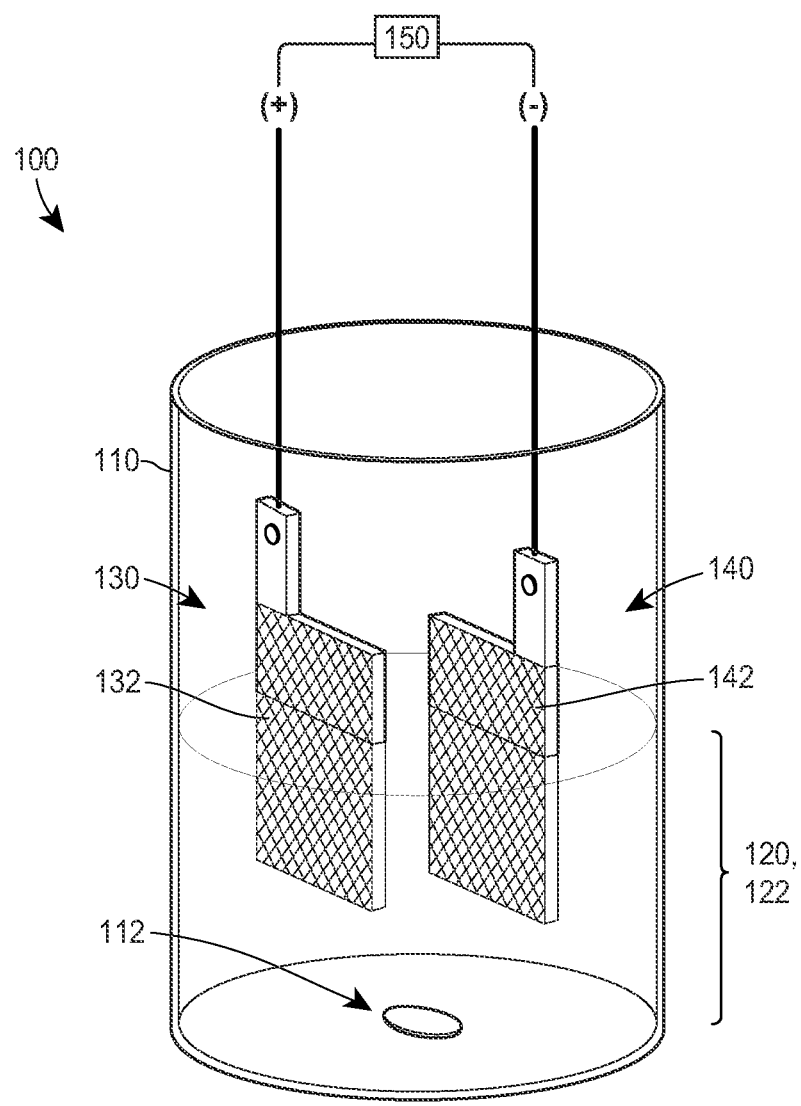
FIG. 1A illustrates a single-cell reactor for pretreating a sample according to the disclosure.
Figure 1B:
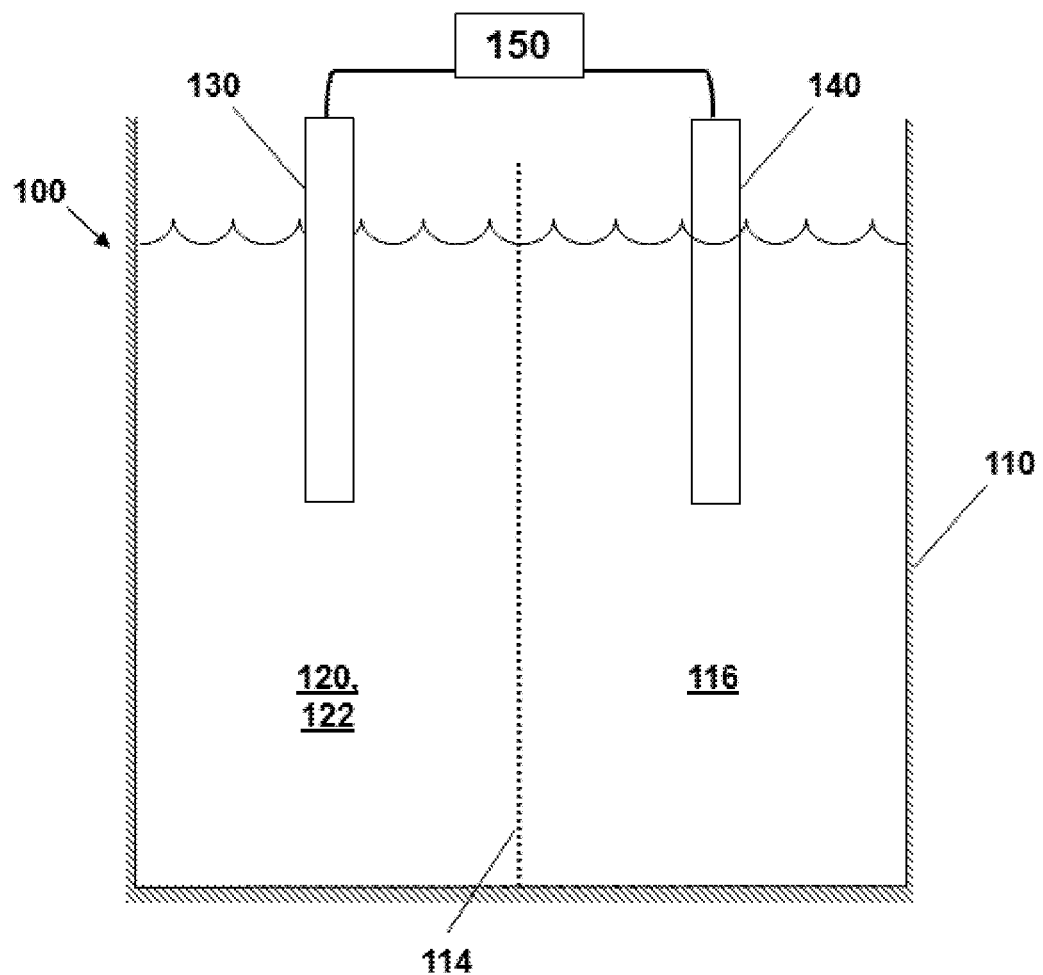
FIG. 1B illustrates a divided-cell reactor for pretreating a sample according to the disclosure.

The disclosure relates to a method for pretreating a sample for metals determination. FIG. 1A and FIG. 1B illustrate an electrochemical reactor 100 for performing the disclosed pretreatment methods. The reactor 100 can include a vessel 110 into which a sample 120 to be pretreated is added, and a stir bar 112 or other mechanical means for stirring/agitating the sample 120 during pretreatment. The sample 120 is suitably an aqueous sample mixture that contains or is suspected of containing one or more metals for detection. The sample or aqueous sample mixture 120 is contacted with a first electrode (anode) 130, which includes electrically conducting boron-doped diamond (BDD), for example in the form of a mesh 132 as illustrated or other structure such as a coated or uncoated perforated plate or porous substrate. The sample or aqueous sample mixture 120 is contacted or electrically contacted with a second electrode (cathode) 140. The second electrode 140 similarly can be in the form of a mesh 142 as illustrated or other structure such as a coated or uncoated perforated plate or porous substrate. As illustrated in FIG. 1A, the second electrode 140 can be in physical contact and electrical with the sample 120, for example in a single-cell design for the reactor 100 and vessel 110. In other embodiments as illustrated in FIG. 1B, the second electrode 140 can be only in electrical contact with the sample 120, for example in a divided-cell design for the reactor 100 and vessel 110 in which the second electrode 140 is physically separated from the sample 120. As illustrated, the second electrode 140 can be immersed in an electrolyte 116 that is separated from the sample 120 via an electrically conductive membrane 114. An electrical potential is applied between the first electrode 130 and the second electrode 140 to provide an electrical current therebetween and through the aqueous sample mixture 120. The electrical current in turn generates hydroxyl ion ($OH^-$) species at the first electrode 130, and oxidizes and frees the one or more metals for detection in the sample 120. This converts the original sample or aqueous sample mixture 120 to a pretreated aqueous sample 122, which includes free metal ions in aqueous solution that correspond to the one or more metals in the original sample 120. The pretreated aqueous sample 122 with the free metal ions in aqueous solution can then be withdrawn from the reactor 100. For example, the pretreated aqueous sample 122 can be analyzed for metal content using any desired conventional analysis technique.

In an embodiment, the disclosure relates to a pre-treatment procedure which will increase the sample digestion efficiency while decreasing assay test length. This is achieved via an electrochemical advanced oxidation process (EAOP) using one or more boron-doped diamond (BDD) electrodes to break down organic constituents in biological samples and release bound metals in various forms as detectable metal ions in solution. This releases the metal ions to be detected by ICP-MS, GF-AAS, or an electroanalytical method such as anodic or cathodic stripping voltammetry (ASV/CSV).

The disclosed method can be adapted to any aqueous sample, whether environmental, biological, or otherwise. Organic metal-chelating agents exist in nearly all real-world samples, in particular environmental and biological samples, and these must be broken down before accurate metal analysis is achieved. Metals that are bound to a chelating agent, regardless of whether they are bound in ionic or other form, are not particularly amenable to detection via a subsequent analytical method, potentially leading to an underestimation of actual metal content/concentration. Certain environmental samples of interest are drinking water, water processed at treatment plants, river/lake/drinking water source locations, etc. Biological samples include whole blood, serum, urine, and saliva, among others.

The sample of interest is mixed with a strong acid such as dilute hydrochloric (HCl) or sulfuric acid ($H_2SO_4$) before being exposed to the BDD electrodes. An anodic current is applied to the BDD electrodes, typically reversing the polarity of the electrodes every 2-5 minutes for 30-120 minutes in a representative single-compartment electrochemical cell. The organic constituents and/or proteins are broken down by the hydroxyl ions generated at the BDD electrodes and the metals are subsequently released and extracted into the dilute acid solution in ionic form. The resulting digestate can then be directly inserted into the analytical instrument of interest and the metals concentration can be determined. Depending on the detection system, multiple metals can be assessed, including, but not limited to, aluminum (Al), arsenic (As), barium (Ba), chromium (Cr), cobalt (Co), cadmium (Cd), mercury (Hg), iron (Fe), lead (Pb), manganese (Mn), nickel (Ni), tin (Sn), vanadium (V), and/or zinc (Zn).

The analysis time and unit cost are significantly decreased compared to the conventional methods listed above (i.e., microwave-assisted digestion and hot-block acid digestion) and are also much more thorough than the simple procedure used by the LEADCARE system (5% HCl mixed in capillary tube). Analytical laboratories with ICP-MS or GF-AAS instrumentation can use the disclosed process as a pretreatment system for a given sample prior to its subsequent analysis for metals concentrations. In a refinement, the electrochemical pretreatment system can be implemented on a microfluidic scale in the digestate product of the method can immediately flow into one of the analysis systems mentioned above. Regardless of the particular embodiment of a corresponding pretreatment apparatus, the ability to expedite the laboratory turnaround time would significantly aid in the medical diagnostic process. The useful knowledge gained by a rapid metals panel to an understanding of exposure routes and diet quality, allows for well-informed medical decisions to be made quickly. Determining the route of exposure with the concurrent ability to measure bodily metal levels clearly enables prediction of potential health risks and associated health outcomes.

Samples

The sample 120 to be pretreated is not particularly limited, and it is generally in the form of an aqueous sample mixture including water as the sample medium. The water can include water present in the original sample, for example in a biological fluid sample, an environmental wastewater sample, or an environmental groundwater sample. The water additional or alternatively can include water added to the sample prior to pretreatment, such as water for dilution of an original liquid sample or for mixing with an original solid or soil sample, such as including an acid therein. In some embodiments, the pretreatment method can include an initial step of sampling or otherwise obtaining the sample 120 to be pretreated, for example by withdrawing a biological sample from a patient or subject, or by sampling/taking an environmental sample from an external/environmental location.

The pretreatment method can be applied to a variety of biological samples. Biological samples can include biological fluid or tissue from a human, other animal, or plant. For example, the biological sample can be a blood sample (e.g., whole blood, serum), a saliva sample, or a urine sample. Some biological sample can include one or more proteins, in particular those that might bind or otherwise limit detection of metals in the sample. For example, the protein can be a metalloprotein or other metal-binding protein typically found in blood or other biological material, which metalloprotein can bind one or more metals of interest such as cobalt, copper, iron, manganese, nickel, zinc. Transferrin is an example of a glycoprotein for bound iron ($Fe^{3+}$) that is normally present in blood. In addition to proteins, biological samples can also include other chelating agents or metal-binding compounds such as citric acid.

The pretreatment method can be applied to a variety of environmental samples. Environmental samples can include solid or liquid samples from the environment to be tested for metals, such as for the purpose of compliance with environmental regulations. The environmental sample can include groundwater, surface water (e.g., fresh or saltwater such as lake, pond, river, stream, swamp, sea, ocean), wastewater (e.g., domestic, commercial, or industrial, such as a stream to/from a wastewater treatment plant), soil, sludge, sediment, leachate (e.g., from a landfill or other waste repository) and/or concrete. When the environmental sample includes a solid material, it is mixed or otherwise diluted with water to form the corresponding aqueous sample mixture, such as with the solid material suspended therein. The environmental sample can include a chelating agent, for example metal-binding or metal-complexing agents such as a weak acid. Example includes ethylenediaminetetraacetic acid (EDTA), citric acid, fulvic acids, or other chelating agents. An environmental sample similarly can include one or more metal-binding components typical of a biological sample (e.g., metalloprotein or other metal-binding protein as described above), for example when the environmental sample includes wastewater or other biological material or waste therein.

Other properties of the sample or aqueous sample mixture 120 are not particularly limited and can vary substantially with the nature/source of the sample 120 to be pretreated. For example, the aqueous sample mixture can substantially free from solids, such as containing less than 10 wt. % solids, such as suspended or dispersed (e.g., non-dissolved) solids, in particular less than 0.1, 1, 2, 5, or 10 wt. % solids. Alternatively or additionally, the aqueous sample mixture can include water as its primary component, such as having at least 80, 90, 95, 98, or 99 wt. % water. The aqueous sample mixture can have a pH value of 4 or less, or 2 or less. The pH can be adjusted to the desired value by adding to the sample 120 a suitable amount of strong (e.g., mineral) acid such as hydrochloric acid, sulfuric acid, nitric acid, phosphoric acid, or another acid such as acetic acid. For example, the sample 120 can be diluted with or have added thereto an acid having a concentration generally ranging from 0.1 M to 5 M. In cases where the sample 120 is naturally acidic and has a sufficiently low pH for electrochemical oxidation of metals in its natural state, no acid need be added. The pH value can represent the initial pH value of the aqueous sample mixture 120 before and/or during electrochemical oxidation. During the pretreatment process, formation of the hydroxyl ions at the BDD electrode can form corresponding peracid species in the aqueous sample mixture 120 being treated. In a divided cell configuration, the pH value can reduce over time during pretreatment as a result of hydrogen ion ($H^+$) generation from water oxidation. The aqueous sample mixture 120 generally does not need to include a supporting electrolyte in solution (although such is possible), because the presence of the acid in the aqueous sample mixture 120 is generally sufficient for electrical conductivity of the mixture.

Metals that can be liberated from a bound form in the original sample 120 via pretreatment according to the disclosure are not particularly limited. Examples of metals that are of particular interest, whether because of their prevalence and/or potential health hazards, include aluminum (Al), antimony (Sb), arsenic (Ar), barium (Ba), bismuth (Bi), cadmium (Cd), chromium (Cr), cobalt (Co), copper (Cu), iron (Fe), gallium (Ga), germanium (Ge), gold (Au), indium (In), lead (Pb), manganese (Mn), mercury (Hg), nickel (Ni), silver (Ag), thallium (Tl), tin (Sn), vanadium (V), and zinc (Zn). In some embodiments, at least one metal of interest is present in the original sample 120. In such embodiments, the effectiveness of the pretreatment method can be expressed as the fraction of total metals present in the original sample 120 in any form that are also present in the pretreated aqueous sample 122 as free metal ions, whether expressed for metals as a whole or for particular metal species. Suitably at least 80, 85, 90, 95, or 98 wt. % and/or up to 90, 95, 98, 99, or 100 wt. % of metals or particular metal species originally present are converted to free metal ions in aqueous solution in the final pretreated sample 122. The foregoing ranges can individually apply to all metal species present collectively as well as individual species. The metals can generally be in any form in the original sample material, for example including free or bound, and ionic or non-ionic, with the purpose of the pretreatment method being to convert the substantially majority of metals to an ionic form where they are free in aqueous solution, which permits them to be detected and/or quantitated with a variety of conventional analytical techniques. In contrast, when in bound or non-ionic form, the metals are generally in unsuitable form for subsequent detection, leading to possible false negative results or substantially lower-than-actual measured concentrations. The metals can be in elemental or metallic form, for example as a pure metal or metal alloy blend. The metals can be in molecular form, for example being covalently or ionically bound to one or more other non-metal atoms (e.g., metal oxides, metal salts, etc. which can be soluble or insoluble in water). The metals can be in an ionic or non-ionic form, but in a chelated, complexed, or otherwise bound form, for example in combination with a metal-binding protein, chelating agent, or other metal-binding agent. The metals can be in a free ionic form in the original sample, in which case they are already in suitable form for subsequent metals analysis, but there is no adverse effect of having them initially present in such form.

Electrochemical Reactor

The particular form and scale of the reactor 100 is not particularly limited. The reactor 100 illustrated in FIG. 1A is representative of a bench-scale reactor 100 and vessel 110 that was used in the examples below. In some embodiments, the pretreatment method can be performed on microfluidic scale in which a very small sample 120 volume is used for pretreatment and analysis, whether as batch sample aliquot or as a part of a continuous flow device. The low sample volumes increase pretreatment speed and reduce total analysis time. For example, the aqueous sample mixture 120 can have a volume in a range from 10 µl to 500 µl, for example at least 10, 20, 50, or 100 µl and/or up to 50, 100, 200, 300, or 500 µl. Such pretreatment can be performed in a correspondingly smaller reactor 100 with smaller electrodes 130, 140 etc.

The boron-doped diamond (BDD) used to form electrodes is not particularly limited and can be formed by conventional techniques, for example being formed/deposited by chemical vapor deposition on a substrate, which can use a deposition source gas including a carbon source (e.g., methane), a boron source (e.g., diborane), and diluent (e.g., one or more of hydrogen, argon, etc.). The chemical vapor deposition (CVD) can be any suitable process, for example a microwave-assisted plasma CVD process. The BDD suitably has a microcrystalline morphology. The boron-doped diamond (BDD) of the first electrode suitably has a carbon:boron (C:B) atomic ratio ranging from 100:1 to 100000:1, for example at least 100:1, 200:1, 500:1, or 1000:1 and/or up to 1000:1, 2000:1, 5000:1, 10000:1, or 100000:1. Relatively lower dopant levels of boron can increase the relative $sp^3$ content of the BDD, while relatively higher dopant levels of boron can increase degree of hydroxyl ion ($OH^-$) species generation at the anode for target analyte oxidation. The BDD generates the hydroxyl ion species at the anode at relatively high voltages and current densities, which species in turn scavenge chelating or other metal-binding groups in the sample, decomposing such groups as well as other proteinaceous, organic, or non-metal materials into gaseous, water-soluble, or ionic species (e.g., $CO_2$, $CO_3^{2-}$, $N_2$, $NO_2^-$ $NH_3$, $NO_3^-$, $ClO_3^-$, $ClO_4^-$, S-containing gases). Decomposition of such metal-binding groups releases any metals therein, allowing the hydroxyl ion species to oxidize the metals (i.e., if not already in the final oxidized form) as well as other metals originally present in the sample in unbound form). The BDD is suitably free of other dopants (e.g., nitrogen, phosphorous), generally having no such other dopants added or being present at other than impurity-level concentrations (e.g., up to 1:1000, 1:10000, or 1:100000 atomic ratio of other dopant or impurity:carbon). In an embodiment, the first electrode 130 is in the form of a substrate upon which the boron-doped diamond (BDD) is coated. The substrate is generally a metal or other material suitable for deposition of BDD thereon, for example including niobium, molybdenum, tantalum, tungsten, or silicon. The substrate can have any desired shape, but it suitably has a relatively high surface area-to-volume ratio to correspondingly provide a relatively higher BDD surface area, hydroxyl ion ($OH^-$) species generation rate, and oxidation rate. For example, the substrate can have a mesh 132 or perforated plate structure to increase surface area and allow circulation of the aqueous sample mixture through the first electrode and in contact with the BDD thereon during operation. In other embodiments, the substrate can include a porous material, for example a porous form of a material suitable for deposition of BDD thereon as described above. In other embodiments, the substrate can be omitted and the first electrode 130 can include a free-standing BDD film or material, for example in the form of a BDD plate.

In an embodiment and as illustrated in FIG. 1A, the aqueous sample mixture 120 can be in direct physical contact with both the first electrode 130 and the second electrode 140 during oxidation. This can represent a single-cell (or single-compartment) electrochemical cell in which the aqueous sample mixture 120 is in direct physical contact and (accordingly) electrical contact with both electrodes 130, 140. The polarity can be switched/cycled between the two electrodes 130, 140 such that each electrode periodically functions as the anode for hydroxyl ion generation and metal oxidation. In such cases, the second electrode 140 suitably additionally includes electrically conducting BDD, for example as a deposition or other coating on a substrate as described for the first electrode 130. In another embodiment and as illustrated in FIG. 1B, the aqueous sample mixture 120 can be in direct physical contact with the first electrode 130, but the aqueous sample mixture 120 is not in direct physical contact with the second electrode 140 during oxidation. This can represent a divided cell (or multi-compartment) electrochemical cell in which the aqueous sample mixture 120 is physically isolated from the second electrode 140, but electrical current can pass through an electrolyte 116 in the second electrode cell, through a membrane 114, and into the aqueous sample mixture 120 in first electrode cell. In this case, the second electrode 140 need not (and suitably does not) include any BDD, for example being formed from any desired electrically conductive material such as stainless steel, silver, nickel, platinum, carbon, lead, lead dioxide, etc. The second cell or compartment which contains the second electrode 140 generally further includes a liquid (e.g., water or water-containing liquid) including a supporting electrolyte 116 such as sodium sulfate, potassium sulfate, sodium nitrate, potassium nitrate, sodium carbonate, or the like. The membrane 114 can be an electrically conductive membrane such as a sulfonated tetrafluoroethylene fluoropolymer (e.g., NAFION) or other (sulfonated) polymer based on polypropylene, poly(tetrafluoroethylene) (PTFE)-type polymer.

Pretreatment

During pretreatment, an electrical potential is applied between the first electrode 130 and the second electrode 140 to provide an electrical current between the electrodes 130, 140 and through the aqueous sample mixture 120. The electrical current can be applied by a power supply 150 or other source of voltage or current in electrical connection with the electrodes 130, 140. The electrical current passing through the sample 120 generates hydroxyl ion ($OH^-$) species at the first electrode 130, which oxidize and free the one or more metals for detection in the sample 120, converting them to free metal ions in solution. This converts the original sample or aqueous sample mixture 120 to a pretreated aqueous sample 122, which includes free metal ions in aqueous solution that correspond to the one or more metals in the original sample 120.

Suitably, the free metal ions in aqueous solution in the pretreated aqueous sample 122 are not subsequently reduced to an elemental metallic form, such as one or more metal elements in a zero oxidation state as a pure metal or alloy blend of multiple metals. Such reduction is suitably not performed or is otherwise prevented/avoided prior to withdrawal of the pretreated aqueous sample (e.g., in an electrochemical cell or other vessel/apparatus including the first and/or second electrodes therein) and/or prior to analysis of the withdrawn pretreated aqueous sample for metal content (i.e., detection of the metal ions in solution). In such embodiments, the pretreated aqueous sample 122 or corresponding cell/vessel 110 is suitably not contacted with and/or does not contain a reducing electrode. In a single-cell electrochemical cell, cycling or reversal of polarity between the first and second electrode can be performed to keep the free metal ions in solution and not plated or otherwise reduced on an electrode surface. In a divided-cell electrochemical cell, the presence membrane can keep the metal ions confined in the first electrode (anode) 130 compartment and accordingly prevent deposition or plating of the metal ions on the second electrode 140 in the other compartment.

After sufficient time for application of the electrical current through the sample, the resulting pretreated aqueous sample 122 with the free metal ions in aqueous solution can be withdrawn from the reactor 100. In some embodiments, the withdrawn pretreated aqueous sample 122 can include one or more non-metal polyatomic ions. The polyatomic ions are suitably anions that are decomposition products from proteinaceous, organic, or non-metal materials in the original sample. Examples include ionic species such as $CO_3^{2-}$, $NO_3^-$, $PO_4^{2-}$ and $ClO_4^-$. The withdrawn pretreated aqueous sample 122 can further include dissolved, water-miscible components such as liquids (e.g., $NH_3$) and/or dissolved gases (e.g., $CO_2$, $N_2$). Such species generally do not interfere with and need not be removed prior to conventional metals analysis techniques. As a result of such decomposition of other non-metal materials in the original sample, the withdrawn pretreated aqueous sample 122 can be directly analyzed in its form as withdrawn, for example without the need for further filtering, separation, purification, or other treatment.

The pretreated aqueous sample 122 can be analyzed for metal content using any desired conventional analysis technique, for example after being withdrawn from the reactor 100. This can be performed by using any suitable conventional technique for metals detection, for example one which uses an aqueous solution of metal ions as an input to an analytical apparatus or system. Representative examples of such apparatus and/or techniques include inductively coupled plasma-mass spectroscopy (ICP-MS), inductively coupled plasma-atomic emission spectroscopy (ICP-AES), graphite furnace-atomic absorption spectroscopy (GF-AAS), electrochemical detection via anodic or cathodic stripping voltammetry (ASV/CSV), etc. The withdrawn pretreated aqueous sample 122 suitably can be used as-is for subsequent metals detection and without separation or purification of the pretreated aqueous sample prior to metals analysis. The withdrawn pretreated aqueous sample 122 can be automatically or directly fed to the metals analytical apparatus, for example as part of an integrated system that pumps or otherwise delivers the sample 122 to the metals analytical apparatus. Alternatively, the withdrawn pretreated aqueous sample 122 can be manually injected or otherwise removed from the reactor 100 and delivered to the metals analytical apparatus.

EXAMPLES

Practical detection of heavy metals in aqueous samples is a challenge for many testing and monitoring stations around the world. Discerning metals from other particles such as biologic material is difficult and often requires sophisticated analytical devices. In certain industries such as healthcare, the results of heavy metal measurements can have a direct impact on patient care. Therefore, generating a quick and reliable measurement of metal concentrations can alter the course of treatment and diagnosis. Heavy metal poisoning is the cause of thousands of deaths and disabilities. Specifically, metals including lead, arsenic, cadmium, and mercury have a direct impact on global health and are listed as four of the World Health Organization's (WHO) "Ten Chemicals of Major Concern" due to their carcinogenic and toxic effect. Lead exposure alone accounted for 494,550 deaths and the loss of 9.3 million disability-adjusted life years (DALYs) in 2015 based on data collected from WHO. Children can absorb four to five times more lead than adults and are more sensitive to the chemical's effects, accounting for mental impairment of 600,000 children annually. Thus, heavy metals toxicology has a wide range of effect and puts large populations at risk.

Currently, blood sampling is used for detection of potentially harmful metals. Blood samples are collected at a physician's office or a local diagnostic center and sent to an external lab for analysis. The first step of analysis is pretreatment of the sample. Typically the blood samples are processed using microwave-assisted digestion (MAD) or acid digestion with heat to break down all organic material in the blood and leave behind the metal ions. After pretreatment, trained lab technicians will conduct inductively coupled plasma-mass spectrometry (ICP-MS) and/or graphite furnace atomic absorption spectroscopy (GF-AAS) to determine the metals concentration in the sample. This processing method is advantageous in the detection method's high sensitively and reliability. However, the process is expensive due to the sample pretreatment step. Standard microwave-digestion systems often cost greater than $30,000 but only require 30 minutes to process a sample. The alternative, acid digestion with heat, is inexpensive but often requires more than 5 hours of processing time. Both pretreatment methods require a substantial sample volume (typically ~1 mL) for analysis. The disclosed method provides a means to pretreat a sample without the use of microwave and/or acid digestion, and it further allows processing of smaller sample volumes (e.g., about 10 µl to 500 µl).

As described above and as generally illustrated in the examples, the disclosed method provides pretreatment for biological and other applicable samples for heavy metal detection. The disclosed pretreatment method increases digestion efficiency and decreases sample turnaround time required to obtain an analytical result. The method uses electrochemical advanced oxidation processes (EAOPs) with boron-doped diamond (BDD) electrodes to breakdown organic material in samples allowing for metal ions to be free in solution. After pretreatment, detection and/or quantitation of a given metal ion can still be achieved using ICP-MS, GF-AAS, or electroanalytical methods such as anodic or cathodic stripping voltammetry (ASV/CSV).

In a representative process, a sample is mixed with dilute hydrochloric (HCl) or sulfuric acid ($H_2SO_4$) and exposed to BDD electrodes with reversing polarity. The electrode polarity can be reversed in 2-5 minute intervals for 30-120 minutes, for example. During this time, organic materials and proteins in the sample are degraded and metals are released into the pretreated sample matrix in a free metal ion form. The free metals are then able to be extracted or otherwise removed from the pretreated sample matrix in the supernatant, which can then be directly inserted into the analytical instrument for examination and the concentration generated. FIG. 1A illustrates an EAOP pretreatment device 100 for performing the method according to the disclosure.

The EAOP pretreatment method utilizes a recycling process to allow for constant production of oxidative power to break down samples and release metal ions. The EAOP method has the power to not only separate ions in solution but break down organic metal-chelating agents to release bound metal ions that would otherwise be undetected. Example 2 below describes an application of the disclosed pretreatment method on bovine whole blood as a sample matrix.

The process utilizes the electrochemical advanced oxidation process to release metal ions and separate them in solution using durable electrodes. The experiment time is shorter than that of acid digestion with heat, the price is significantly decreased relative to MAD, and a typical sample volume (e.g., about 100 µL) is considerably decreased compared to conventional techniques. Compared to a similar technology such as LEADCARE, the EAOP pretreatment system is more comprehensive and reliable with a reduced risk of underestimating lead concentrations. Laboratories with ICP-MS or GF-AAS capability can utilize the pretreated sample as an input to the analytical system for metal ion detection and quantitation. Alternatively, a table-top analytical device can include a microfluidic system to perform the pretreatment method, whereupon the digestate can then immediately flow into one of the analysis systems mentioned above.

The disclosed procedure can be adapted to any aqueous sample, whether it be environmental or biological. Organic metal-chelating agents exist in nearly all real-world samples and these must be broken down before accurate metal analysis is achieved. Certain environmental samples of interest are drinking water, water processed at treatment plants, river/lake/drinking water source locations, etc. Biological samples include whole blood serum, urine, and saliva among others. Depending on the detection system, multiple metals can be assessed including but now limited to: Aluminum (Al), Arsenic (As), Barium (Ba), Chromium (Cr), Cobalt (Co), cadmium (Cd), Mercury (Hg), Iron (Fe), Lead (Pb), Manganese (Mn), Nickel (Ni), Tin (Sn), Vanadium (V), and zinc (Zn).

Examples 1 and 2 illustrate the disclosed methods for pretreatment of samples for metals determination, in particular demonstrating the ability of the disclosed methods to release chelated/bound metals as free metal ions and to pretreat complex sample matrices such as biological samples.

Figure 2A:
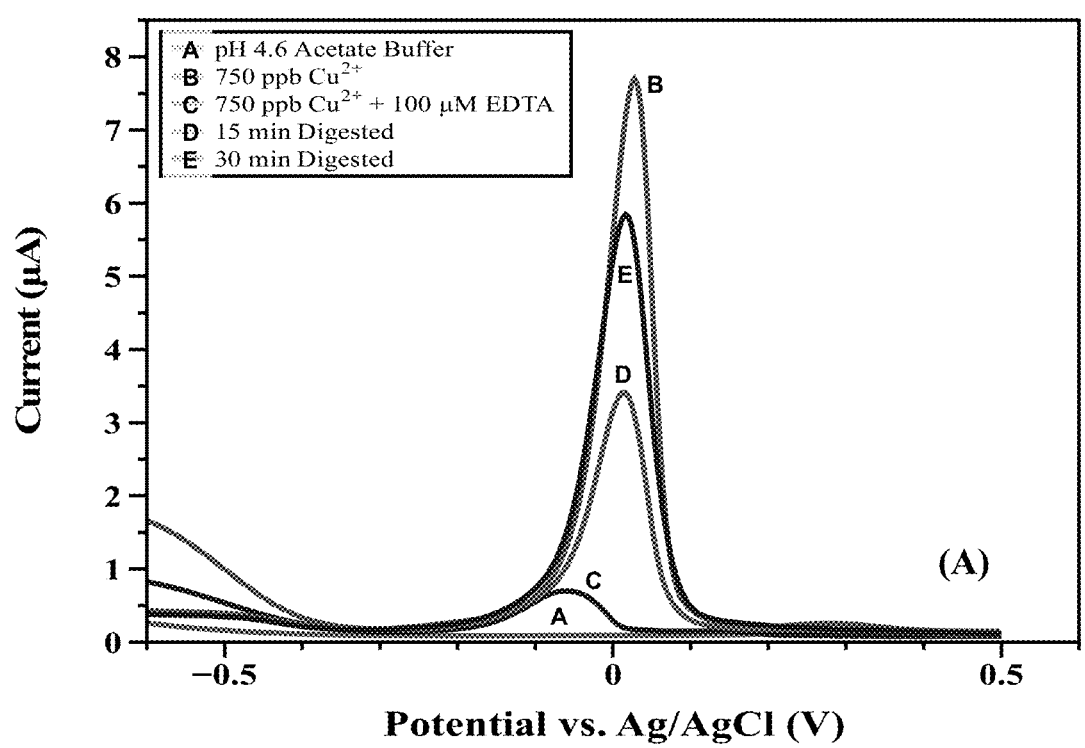
FIG. 2A shows stripping voltammograms obtained before, during, and after the process of treating a buffered sample containing a Copper-Ethylenediaminetetraacetic acid (Cu-EDTA) complex.
Figure 2B:
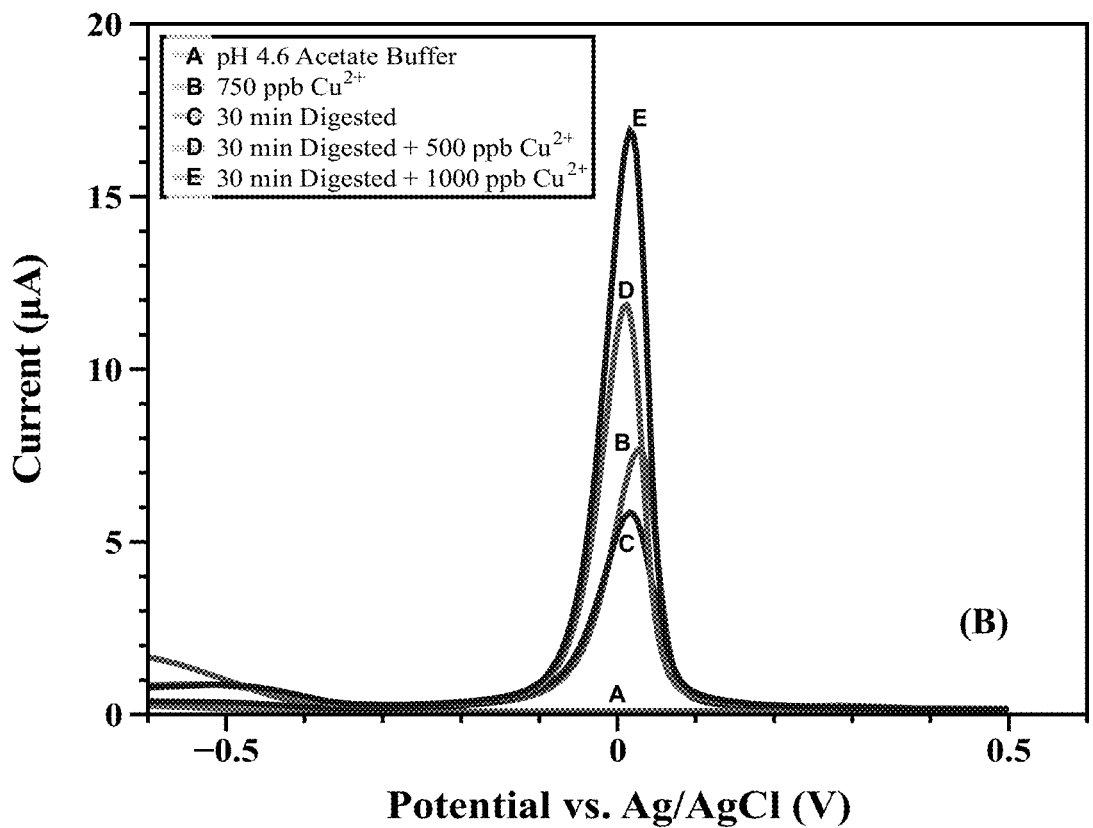
FIG. 2B shows stripping voltammograms completed on the 30-minute digested sample of FIG. 2A completed for a standard addition experiment.
Figure 2C:
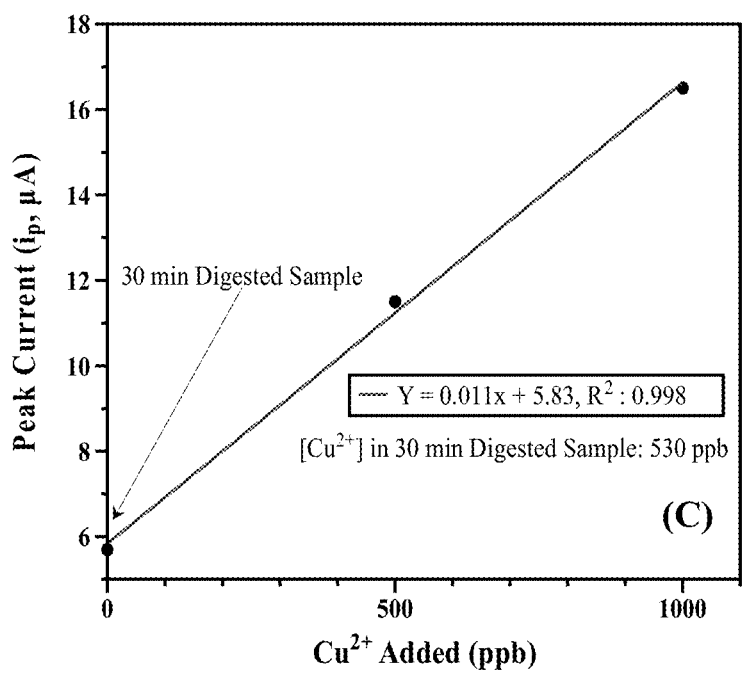
FIG. 2C shows the calibration curve resulting from the standard addition analysis of FIG. 2B.

Example 1—Pretreatment of a Sample Containing Bound Metals for Subsequent Metals Determination Examples completed in buffered samples containing bound/chelated metals are illustrated in FIGS. 2A-2C and demonstrated the capability of BDD electrodes to electrochemically break down metal-organic complexes.

FIG. 2A shows stripping voltammograms (on BDD) obtained before, during, and after the process of treating a buffered sample containing a Copper-Ethylenediaminetetraacetic acid (Cu-EDTA) complex. Trace "B" in FIG. 2A shows the initial response from 750 ppb $Cu^{2+}$ free in solution before adding EDTA. After addition of EDTA, it can then be seen in trace "C" that the response is substantially diminished, indicating formation of the Cu-EDTA complex (i.e., where the copper ions are bound and no longer free in solution). BDD electrodes were then placed in solution and a current density of 40 $mA/cm^2$ was applied, reversing the polarity each minute. Traces "D" and "E" in FIG. 2A show the recovery of the $Cu^{2+}$ peak as the treatment ("digestion") progresses for 15 or 30 minutes, respectively, signifying (i) the cleavage of the Cu-EDTA bond to release $Cu^{2+}$ as free ions in solution for detection and (ii) the oxidative decomposition of EDTA into $CO_2$ and other oxidation products preventing further binding of metals by the EDTA. After 30 minutes, 80% of the original copper response was obtained.

FIGS. 2B and 2C show a standard addition experiment completed on the 30-minute digested sample. Aliquots of $Cu^{2+}$ standard were added to the sample to verify the final concentration. A $[Cu^{2+}]$ value of 530 ppb was obtained, yielding a 72% recovery of free $Cu^{2+}$ ions after 30 minutes of treatment time.

While these experiments were completed in buffered samples, the results obtained are directly applicable to disclosed methods. Organic chelating agents and proteins bind with metal ions in the body, rendering them undetectable by electrochemical methods (such as ASV or CSV) or by other analytical methods directed to detection of free metal ions in solution. The ability to breakdown such metal complexes with EAOPs provides a rapid, efficient mode of metal ion release for detection of otherwise bound metals in biological or other sample fluids.

Example 2—Pretreatment of a Whole Blood Sample for Subsequent Metals Determination Biological samples at varying dilutions were pretreated according to the disclosure.

Bovine whole blood was diluted 1:5 in 1.0 M sulfuric acid ($H_2SO_4$) in a total volume of 50 mL. BDD electrodes were placed into the blood-acid slurry and 40 $mA/cm^2$ was applied to break down the organic chelating agents and proteins. This current density was chosen based on a process in which EAOPs were used to extract metals from solid samples such as slag, coal, and ash that was dissolved in $H_2SO_4$. Upon application of anodic current, the blood acid solution began to bubble significantly, most likely due to the generation of $H_2$ gas at the cathode and the $CO_2$ generated by organic oxidation. The bubbling became too severe after a 1-hour treatment period, and the experiment was stopped.

Figure 3:
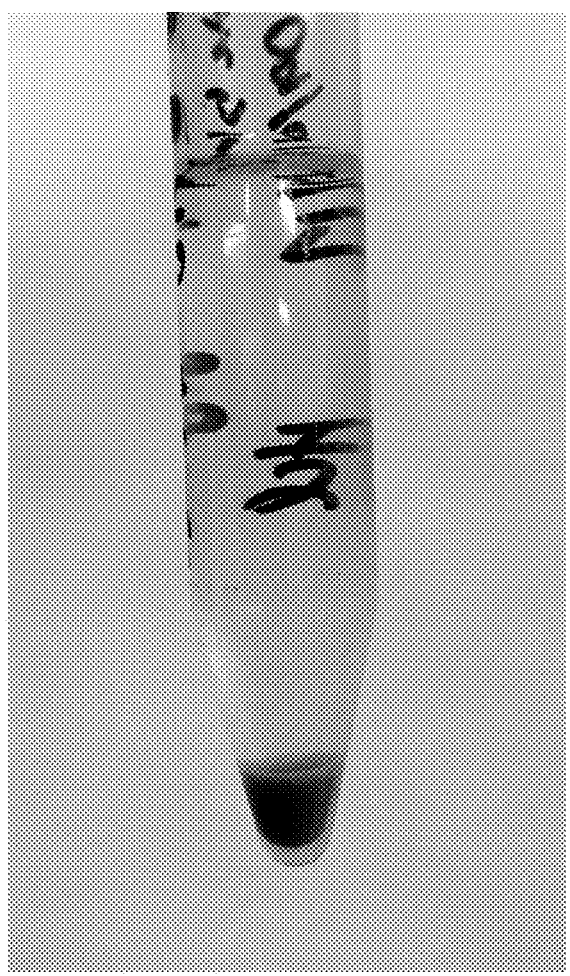
FIG. 3 is a photo showing a final digestion product of a bovine whole blood sample using the pretreatment method according to the disclosure.

Another experiment was completed with bovine whole blood using a stronger acid, hydrochloric acid (HCl) at a concentration of 5.0 M. The solution volume was also decreased to 15 mL and the blood:acid ratio decreased to 1:10. The polarity of the BDD electrodes was changed every 5 min to avoid metal deposition on the cathode surface and the experiment was run for a total of 2 hours. The final digestion product is shown in FIG. 3, which includes a small portion of solids at the base and a large, clear supernatant suitable for subsequent metals analysis. This experiment shows that the pretreatment conditions could be altered to prevent undesirable foaming to obtain a suitable clarified sample for subsequent analysis without the addition of an anti-foaming agent.

Because other modifications and changes varied to fit particular operating requirements and environments will be apparent to those skilled in the art, the disclosure is not considered limited to the example chosen for purposes of illustration, and covers all changes and modifications which do not constitute departures from the true spirit and scope of this disclosure.

Accordingly, the foregoing description is given for clearness of understanding only, and no unnecessary limitations should be understood therefrom, as modifications within the scope of the disclosure may be apparent to those having ordinary skill in the art.

All patents, patent applications, government publications, government regulations, and literature references cited in this specification are hereby incorporated herein by reference in their entirety. In case of conflict, the present description, including definitions, will control.

Throughout the specification, where the compounds, compositions, articles, methods, and processes are described as including components, steps, or materials, it is contemplated that the compositions, processes, or apparatus can also comprise, consist essentially of, or consist of, any combination of the recited components or materials, unless described otherwise. Component concentrations can be expressed in terms of weight concentrations, unless specifically indicated otherwise. Combinations of components are contemplated to include homogeneous and/or heterogeneous mixtures, as would be understood by a person of ordinary skill in the art in view of the foregoing disclosure.

What is claimed is:

1. A method for pretreating a sample for metals determination, the method comprising:
   providing an aqueous sample mixture comprising a sample containing or suspected of containing one or more metals for detection;
   contacting the aqueous sample mixture with a first electrode comprising electrically conducting boron-doped diamond (BDD);
   electrically contacting the aqueous sample mixture with a second electrode;
   applying an electrical potential between the first electrode and the second electrode (i) to provide an electrical current therebetween and through the aqueous sample mixture, (ii) to generate hydroxyl ion ($OH^-$) species at the first electrode, (iii) to oxidize and free the one or more metals for detection in the sample, thereby forming a pretreated aqueous sample comprising free metal ions in aqueous solution and corresponding to the one or more metals in the original sample, wherein the aqueous sample mixture is in direct physical contact with the first electrode, and the aqueous sample mixture is not in direct physical contact with the second electrode during oxidation; and
   withdrawing the pretreated aqueous sample comprising the free metal ions in aqueous solution;
   wherein:
   the pretreated aqueous sample is formed in an electrochemical cell from which the pretreated aqueous sample is withdrawn;
   there is no reduction or plating of metals prior to withdrawal of the pretreated aqueous sample and during application of the electrical potential; and
   there is no reduction or plating of metals subsequent to withdrawal of the pretreated aqueous sample.

2. A method for pretreating a sample for metals determination, the method comprising:
   providing an aqueous sample mixture comprising a sample containing or suspected of containing one or more metals for detection, wherein the aqueous sample mixture is substantially free from solids;
   contacting the aqueous sample mixture with a first electrode comprising electrically conducting boron-doped diamond (BDD);
   electrically contacting the aqueous sample mixture with a second electrode;
   applying an electrical potential between the first electrode and the second electrode (i) to provide an electrical current therebetween and through the aqueous sample mixture, (ii) to generate hydroxyl ion ($OH^-$) species at the first electrode, (iii) to oxidize and free the one or more metals for detection in the sample, thereby forming a pretreated aqueous sample comprising free metal ions in aqueous solution and corresponding to the one or more metals in the original sample; and
   withdrawing the pretreated aqueous sample comprising the free metal ions in aqueous solution;
   wherein:
   the pretreated aqueous sample is formed in an electrochemical cell from which the pretreated aqueous sample is withdrawn;
   there is no reduction or plating of metals prior to withdrawal of the pretreated aqueous sample and during application of the electrical potential; and
   there is no reduction or plating of metals subsequent to withdrawal of the pretreated aqueous sample.

3. A method for pretreating a sample for metals determination, the method comprising:
   providing an aqueous sample mixture comprising a biological sample containing or suspected of containing one or more metals for detection;

contacting the aqueous sample mixture with a first electrode comprising electrically conducting boron-doped diamond (BDD);

electrically contacting the aqueous sample mixture with a second electrode;

applying an electrical potential between the first electrode and the second electrode (i) to provide an electrical current therebetween and through the aqueous sample mixture, (ii) to generate hydroxyl ion ($OH^-$) species at the first electrode, (iii) to oxidize and free the one or more metals for detection in the sample, thereby forming a pretreated aqueous sample comprising free metal ions in aqueous solution and corresponding to the one or more metals in the original sample; and withdrawing the pretreated aqueous sample comprising the free metal ions in aqueous solution;

wherein:
the pretreated aqueous sample is formed in an electrochemical cell from which the pretreated aqueous sample is withdrawn;
there is no reduction or plating of metals prior to withdrawal of the pretreated aqueous sample and during application of the electrical potential; and
there is no reduction or plating of metals subsequent to withdrawal of the pretreated aqueous sample.

4. The method of claim 1, wherein the sample comprises a biological sample.

5. The method of claim 3, wherein the biological sample is selected from the group consisting of a blood sample, a saliva sample, and a urine sample.

6. The method of claim 3, wherein the biological sample is a blood sample.

7. The method of claim 3, wherein the biological sample comprises a protein.

8. The method of claim 1, wherein the sample comprises an environmental sample.

9. The method of claim 8, wherein the environmental sample is selected from the group consisting of groundwater, surface water, wastewater, soil, sediment, concrete, leachate, and combinations thereof.

10. The method of claim 8, wherein the environmental sample comprises a chelating agent.

11. The method of claim 1, wherein the aqueous sample mixture is substantially free from solids.

12. The method of claim 1, wherein the aqueous sample mixture has a pH value of 4 or less.

13. The method of claim 1, wherein the one or more metals for detection are selected from the group consisting of aluminum (Al), antimony (Sb), arsenic (Ar), barium (Ba), bismuth (Bi), cadmium (Cd), chromium (Cr), cobalt (Co), copper (Cu), iron (Fe), gallium (Ga), germanium (Ge), gold (Au), indium (In), lead (Pb), manganese (Mn), mercury (Hg), nickel (Ni), silver (Ag), thallium (Tl), tin (Sn), vanadium (V), zinc (Zn), and combinations thereof.

14. The method of claim 1, wherein:
the sample contains the one or more metals for detection;
the sample contains at least one of a metal-binding protein with bound metal ions and a chelating agent with bound metal ions; and
at least 80 wt. % of total metals present in the original sample in any form are present in the pretreated aqueous sample as free metal ions.

15. The method of claim 1, wherein the boron-doped diamond (BDD) of the first electrode has a carbon:boron (C:B) atomic ratio ranging from 100:1 to 100000:1.

16. The method of claim 1, wherein the first electrode further comprises a substrate upon which the boron-doped diamond (BDD) is coated.

17. The method of claim 1, wherein the first electrode comprises a free-standing boron-doped diamond (BDD) material.

18. The method of claim 1, wherein the aqueous sample mixture is in direct physical contact with both the first electrode and the second electrode during oxidation.

19. The method of claim 1, wherein the aqueous sample mixture is in direct physical contact with the first electrode, and the aqueous sample mixture is not in direct physical contact with the second electrode during oxidation.

20. The method of claim 1, wherein the withdrawn pretreated aqueous sample further comprises one or more non-metal polyatomic ions.

21. The method of claim 1, wherein the free metal ions in aqueous solution in the pretreated aqueous sample are not subsequently reduced to an elemental metallic form.

22. The method of claim 1, wherein the aqueous sample mixture has a volume in a range from 10 µl to 500 µl.

23. The method of claim 1, further comprising:
analyzing the withdrawn pretreated aqueous sample for metal content by a method selected from the group consisting of inductively coupled plasma (ICP), mass spectroscopy (MS), atomic emission spectroscopy (AES), atomic absorption spectroscopy (AAS), and combinations thereof.

24. The method of claim 1, further comprising:
withdrawing a gaseous byproduct stream.

25. The method of claim 1, wherein:
the second electrode comprises electrically conducting boron-doped diamond (BDD); and
the method comprises cycling polarity between the first electrode and the second electrode when forming the pretreated aqueous sample to oxidize metals in the sample while preventing metal deposition and plating.

* * * * *